US009018441B2

(12) United States Patent
Wildt (10) Patent No.: US 9,018,441 B2
(45) Date of Patent: Apr. 28, 2015

(54) HAIRLESS NOD SCID MOUSE (75) Inventor: Sheryl Wildt, Indianapolis, IN (US)

(73) Assignee: Harlan Laboratories, Inc., Indianapolis, IN (US)

(*) Notice: Subject to any disclaimer, the term of this patent is extended or adjusted under 35 U.S.C. 154(b) by 63 days.

(21) Appl. No.: 13/640,522

(22) PCT Filed: Apr. 14, 2011

(86) PCT No.: PCT/US2011/032494
§ 371 (c)(1),
(2), (4) Date: Dec. 21, 2012

(87) PCT Pub. No.: WO2011/130512
PCT Pub. Date: Oct. 20, 2011

(65) Prior Publication Data
US 2013/0205417 A1 Aug. 8, 2013

Related U.S. Application Data (60) Provisional application No. 61/324,030, filed on Apr. 14, 2010, provisional application No. 61/391,444, filed on Oct. 8, 2010.

(51) Int. Cl.
*A01K 67/027* (2006.01)
*C07K 14/47* (2006.01)
*C12N 15/85* (2006.01)

(52) U.S. Cl.
CPC ......... *A01K 67/0278* (2013.01); *A01K 67/0276* (2013.01); *A01K 2217/075* (2013.01); *A01K 2217/15* (2013.01); *A01K 2227/105* (2013.01); *A01K 2267/0381* (2013.01); *A01K 2267/0387* (2013.01); *C07K 14/4702* (2013.01); *C12N 15/8509* (2013.01)

(58) Field of Classification Search
CPC .................... A01K 2227/105; A01K 67/0271; A01K 2217/05; A01K 2267/03; A01K 2267/0337; A01K 67/0275; A01K 2217/075; A01K 2217/00; A01K 2217/15; A01K 2267/0325; A01K 2267/0387
See application file for complete search history.

(56) References Cited

U.S. PATENT DOCUMENTS

2009/0235372 A1* 9/2009 Clifford et al. ................. 800/18

FOREIGN PATENT DOCUMENTS

WO WO 2005/090968 9/2005

OTHER PUBLICATIONS

Greiner et al, Stem Cells, 1998, 16:166-177.*
Liang et al, "Characterization of a New Hairless SCID Mouse", 2009 Abstract No. 3218, In: Proceedings of the 9th Annual Meeting of the American Association for Cancer Research.*
Shultz et al, J Immunol, 1995, 154:180-191.*
Morrissey et al, J Immunol, 1980, 125:1558-1562.*
Heusch et al, Eur J Immunol, 2004, 34:1861-1869.*
PCT Search Report and Written Opinion prepared for PCT/US2011/032494, mailed Jun. 16, 2011.
Greiner, Dale L., et al., "SCID Mouse Models of Human Stem Cell Engraftment", 1998, Stem Cells, No. 16, pp. 166-177.
Niclou, Simone P., et al., "A Novel eGFP-Expressing Immunodeficient Mouse Model to Study Tumor-Host Interactions", Sep. 2008, The FASEB Journal, vol. 22, pp. 3120-3128.
Hoffman, Robert M., et al., "Whole-Body Imaging With Fluorescent Proteins", 2006, Nature Protocols, vol. 1, No. 3, pp. 1429-1438.
Williams, Shanice V., et al., "The SHrN Hairless NOD Mouse Model: Development and Characterization", 2010, Abstract No. 393, In: Proceedings of the 10th Annual Meeting of the American Association for Cancer Research.
"The Researcher", Mar. 2010, XP055084859, Retrieved from the Internet: URL: https://webapps.harlan.com/theresearcher/archives/issue_30_03_10/researcher.pdf [retrieved on Oct. 22, 2013].
Shultz L D et al: "Humanized mice in translational biomedical research", The Journal of Immunology, Nature Pub. Group, vol. 7, No. 2, Feb. 2007, pp. 118-130, XP002493022, ISSN: 1474-1733, DOI: 10.1038/NRI2017.
"Choosing an Immunodeficient mouse model", Jax Notes, 2006, pp. 1-16, XP055085001, Retrieved from the Internet: URL:http://jaxmice.jax.org/jaxnotes/archive/501.pdf [retrieved on Oct. 23, 2013].
Troy T et al: "Quantitative Comparision of the Sensitivity of Detection of Fluorescent and Bioluminscent Reporters in Animal Models", Molecular Imaging, MIT Press, US, vol. 3, No. 1, Jan. 2004, pp. 9-23, XP009049182, ISSN: 1535-3508, DOI: 10.1162/153535004773861688.
D. Monti et al., "Effect of different terpene-containing essential oils on permeation of estradiol through hairless mouse skin", International Journal of Pharmaceutics, vol. 237, No. 1-2, Apr. 2002, pp. 209-214, XP055084960, ISSN: 0378-5173, DOI:10.1016/S0378-5173(02)00032-7.
Song Yanqui et al. (2007), "Establishment of K652/NOD-SCID Mouse Leukemia Model," Chinese Journal of Hematology, vol. 15(1) pp. 16-19 (English abstract provided).
San Jose at al (2001), "The thymus of the hairless rhino-j (hr/hr-j) mice," Journal of Anatomy, vol. 198(4): pp. 399-406.

* cited by examiner

*Primary Examiner* — Valarie Bertoglio
*Assistant Examiner* — Chi-Feng Hsu
(74) *Attorney, Agent, or Firm* — Barnes & Thornburg LLP (57) ABSTRACT Hairless, immunodeficient mice on a non-obese diabetic (NOD) background and methods for their production are disclosed herein. The mice are hairless and have multiple immunodeficiencies, including B-cell and T-cell deficiencies, as well as impaired macrophage and complement function. The mice also have a further deficit in natural killer and dendritic cells of the immune system. The mice are useful for biomedical research, for example, in studies involving xenograft transplantation, spontaneous tumors, cancer cell tumorigenesis, tumor angiogenesis, tumor metastatic potential, tumor suppression therapy, carcinogenesis regulation, and tumor imaging.

2 Claims, 11 Drawing Sheets

HAIRLESS NOD SCID MOUSE

CROSS-REFERENCE TO RELATED APPLICATIONS

This application is a national stage entry under 35 USC §371(b) of International Application No. PCT/US2011/032494, filed Apr. 14, 2011, which claims priority under 35 U.S.C. §119(e) to U.S. Provisional Application Ser. No. 61/324,030, filed on Apr. 14, 2010, and U.S. Provisional Application Ser. No. 61/391,444, filed on Oct. 8, 2010, the entire disclosures of all of which are incorporated herein by reference.

TECHNICAL FIELD

The present disclosure pertains generally to biomedical research. More specifically, the present disclosure pertains to a mouse with genetic advantages for biomedical research.

BACKGROUND AND SUMMARY

There are hundreds of pathological mutants in mice and rats, and many of these are of interest to biomedical research. Mutant mice are typically used for specialized research and development projects. Mutant mice can be maintained with either outbred or inbred genetic backgrounds, the properties of which confer genetic advantages and disadvantages. For example, the athymic nude gene on the outbred HsdCpb:NMRI background produces a relatively robust animal, but the same mutation in mice having a BALB/cOlaHsd background produces a less robust animal.

$Prkdc^{scid}$ is a mutation of the gene encoding the catalytic subunit of DNA activated protein kinase (Prkdc) that results in a severe combined immunodeficiency (scid) (for review, see Bosma and Carroll, 1991). It is an autosomal recessive mutation that disrupts the differentiation of B-cell and T-cell progenitor cells due to a defective variable, diversity and joining (VDJ) recombinase system necessary for generating B- and T-cell receptors. Mice with a Prkdc mutation lack Thy-1-positive dendritic epidermal cells. Unlike nude mice, $Prkdc^{scid}$ mutant mice posses a thymus and lymph nodes.

The non-obese diabetic (NOD) mouse is an animal model of Type 1 diabetes, exhibiting a susceptibility to spontaneous development of autoimmune, T cell-mediated insulin-dependent diabetes mellitus (IDDM). The NOD strain and related strains were developed at Shionogi Research Laboratories in Aburahi, Japan, by Makino and colleagues and first reported in 1980 (Makino et al., 1980). Additionally, NOD strains are typically characterized by a functional deficit in natural killer (NK) cells, defects in myeloid development and function as well as in the differentiation and function of antigen presenting cells (APCs), and a C5 deficiency that inhibits activation of both classical and alternative pathways of hemolytic complement (Greiner et al., 1998).

Mouse strains carrying a $Prkdc^{scid}$ mutation, while displaying a lack of B- and T-cell function, express normal levels of NK cells, hemolytic complement and myeloid function. In addition, $Prkdc^{scid}$ mutants on various background strains produce immunoglobulin and functional T-cells at low levels as the mice age, a phenomenon referred to as "leakiness." These innate immune properties are disadvantageous for certain research applications, especially engraftment of human tumor cell lines.

The $Prkdc^{scid}$ mutation has been transferred from the C.B-17 background onto the diabetes susceptible nonobese diabetic (NOD) background and is referred to as the NOD scid. Unlike the typical NOD mouse, development of autoimmune diabetes does not occur due to lack of T-cell function. NOD scid mice are further characterized by a NK cell functional deficit, macrophage deficiency, and a lack of detectable hemolytic complement (Greiner et al., 1998).

In addition, the "leaky" phenotype of homozygous scid mice, resulting from the incomplete blocking of VDJ recombinase activity that leads to residual B- and T-cell activity, is suppressed in this model compared to other scid mice on various genetic backgrounds. These characteristics are advantageous for studies involving long-term growth of transplanted cells. For example, human cell lines such as PC-3 and DU145, and CD-34 positive stem cells may effectively be grown long-term in NOD scid mice, but not in other scid mice that exhibit normal NK cell function, macrophages, and circulating complement that may influence tumor growth or engraftment of human stem cells. The immunologic profile of the NOD scid mouse renders it useful for biomedical research in oncology, immunology, hematology, HIV pathology, and other fields.

Despite their suitability for numerous applications, NOD scid mice exhibit some characteristics that can be disadvantageous for certain research purposes. For example, NOD scid mice have a full coat of albino hair, so their hair must be shaved prior to inoculation of cells, and subsequent visualization and imaging of tumors is more difficult than in a hairless model. Further, even after shaving a haired mouse, hair follicles remain which may autofluoresce and interfere with imaging studies employing bioluminescent and fluorescent reporters. The hairless homozygous mutant, unlike the nude mouse, is devoid of hair follicles (Lyon et al., 1996) thereby eliminating the autofluorescence from follicles that occurs in other xenograft models.

Described herein are improvements to the NOD scid mouse made by crossing NOD scid mice with a mouse carrying a mutation in the hairless gene (Hr) and backcrossing onto the NOD scid genetic background to produce a hairless NOD scid mouse strain. The hairless NOD scid mice disclosed herein are particularly advantageous for the studies of xenograft transplantation, spontaneous tumors, cancer cell tumorigenesis, tumor angiogenesis, tumor metastatic potential, tumor suppression therapy, carcinogenesis regulation, tumor imaging, and human stem cell engraftment.

The following various embodiments are contemplated:

1) A hairless, immunodeficient mouse on a non-obese diabetic (NOD) background having B-cell, T-cell, NK-cell, macrophage and complement deficiency.

2) The mouse of clause 1, wherein the mouse is homozygous for a Prkdc allele.

3) The mouse of clause 2, wherein the Prkdc allele is scid ($Prkdc^{scid}$).

4) The mouse of any of clauses 1 to 3, wherein the mouse is homozygous for an Hr allele.

5) The mouse of clause 4, wherein the Hr allele is hr ($Hr^{hr}$).

6) The mouse of any of clauses 1 to 5, wherein the non-obese diabetic background is NOD.CB17-$Prkdc^{scid}$.

7) The mouse of any of clauses 1 to 5, wherein the non-obese diabetic background is NOD.CB17-$Prkdc^{scid}$/NCrHsd.

8) The hairless mouse of any of clauses 1 to 7 further having a dendritic cell deficiency, wherein the dendritic cell deficiency is a reduction in the number of dendritic cells compared to an immunodeficient mouse of the same background that is not hairless.

9) A method of producing a hairless, immunodeficient mouse on a non-obese diabetic (NOD) background, the method comprising:

(a) crossing a NOD scid mouse strain homozygous for a Prkdc allele with a second mouse strain homozygous for an Hr allele to produce progeny heterozygous for both the Hr allele and the Prkdc allele;

(b) intercrossing the heterozygous progeny produced from step (a) with NOD scid mice;

(c) selecting offspring of step (b) that are homozygous for the Prkdc allele and have a genotype that is more similar to NOD scid;

(d) crossing the offspring selected in step (c) with mice homozygous or heterozygous for the Hr allele.

10) The method of clause 9 wherein the Prkdc allele is scid ($Prkdc^{scid}$).

11) The method of any of clauses 9 to 10 wherein the Hr allele is hr ($Hr^{hr}$).

12) The method of any of clauses 9 to 11, wherein the progeny produced from step (a) are genotyped using a process selected from the group consisting of:

single nucleotide polymorphism allelic discrimination, polymerase chain reaction, and single nucleotide polymorphism profiling.

13) The method of any of clauses 9 to 12, wherein the NOD scid mouse of steps (a) and (b) is a NOD.CB17-$Prkdc^{scid}$ mouse.

14) The method of any of clauses 9 to 12, wherein the NOD scid mouse of steps (a) and (b) is a NOD.CB17-Prkdcscid/NCrHsd-$Prkdc^{scid}$ mouse.

15) The method of any of clauses 9 to 14 wherein the second mouse strain of step (a) is an MF-1-hr mouse.

DETAILED DESCRIPTION

While the invention is susceptible to various modifications and alternative forms, specific embodiments will herein be described in detail. It should be understood, however, that there is no intent to limit the invention to the particular forms described, but on the contrary, the intention is to cover all modifications, equivalents, and alternatives falling within the scope of the invention.

The following terms as used throughout the specification are intended to have the meaning set forth below:

As used herein, the phrase "more similar to NOD scid" refers to mice within a particular generation that possess a genotype that is more like the NOD scid strain than other mice of the same generation possess. This can be quantified, for example, by single nucleotide polymorphism analysis.

Disclosed herein is the production of a hairless NOD scid mouse. Hairless NOD scid mice are particularly advantageous for biomedical research and development experiments utilizing xenograft transplantation, spontaneous tumors, cancer cell tumorigenesis, tumor angiogenesis, tumor metastatic potential, tumor suppression therapy, carcinogenesis regulation, tumor imaging, and human stem cell engraftment.

NOD scid Mouse

The $Prkdc^{scid}$ mutation has been transferred from the C.B-17 background onto the diabetes susceptible nonobese diabetic (NOD) background and is referred to as the NOD scid. The NOD scid mutant mouse was received by National Cancer Institute, Frederick, Md. in 2004 from National Institutes of Health, Bethesda, Md. NOD scid have severe combined immunodeficiency (scid) affecting T- and B-cell development. Unlike the typical NOD mouse, development of autoimmune diabetes does not occur due to lack of T-cell function. NOD scid mice are further characterized as having a NK cell functional deficit, macrophage deficiency, and absence of circulating complement. NOD scid mice are susceptible to opportunistic pathogens and have an increased incidence of thymic lymphomas with age.

Hairless (Hr) Mouse

Homozygous (hr/hr) mice have normal coat until about 10 days of age, at which time hair loss commences. Although sparse hair growth occurs at monthly intervals, the mice are essentially hairless by 5-6 weeks of age. The complete hair is lost from the follicle (Crew and Mirskaia, 1931). The vibrissae are repeatedly shed and become more abnormal with age. The hairless gene is a thyroid-hormone responsive gene and corepressor for thyroid hormone receptors, mediating thyroid hormone action in the brain and skin (Potter et al., 2001). Their toenails are frequently long and curved.

Generally, special husbandry procedures are not required to maintain hairless mice. With the exception of occasional skin abscesses, they generally show no increased susceptibility to infection. However, hairless mice do have a mild immune deficiency, possibly due to defects of T-helper cells (Reske-Kunz et al., 1979). There is a high incidence of leukemia in hr/hr compared with hr/+ mice (Heiniger et al., 1974) associated with immunological defects and impaired graft-versus-host (GVH) response (L'Anson and Gasser, 1973). An association between defective immune function and lymphomagenesis in hairless mice may be due to the reduced immune responsiveness of this mutant to syngeneic lymphoma cells, and to purified murine leukemia virus (MuLVs) (Johnson and Meier, 1981). In addition, splenic T cells from this mutant have been shown to have a depressed proliferative response to I-region alloantigens (Morrissey et al., 1980). Further, an inversion in the normal proportions of Ly-1+ and Ly-123+ T cells has been found in spleens (Reske-Kunz et al., 1979).

Histopathologically, hairless mice have hyperkeratosis of the stratified epithelium upper part of the hair canals beginning at about 14 days. Hair club formation is abnormal, with the internal root sheath coalescing around the terminal part of the hair shaft so that the lower part of the hair sheath fails to follow the ascending hair club and becomes stranded in the dermis. Cysts develop from two sources, the hyperkarotic upper part of the hair canals, and the sheaths of the abnormal follicles stranded in the dermis (Fraser, 1946; Mann, 1971). Glomerular changes in hairless mice have been described by Fukui et al., 1975. Hairless mice are fertile, but most females do not nurse their young well. The most effective breeding system uses homozygous mutant males and heterozygous females (ILAR, 1989).

The presence of NK cell, macrophage, and complement function can influence initial tumor growth and metastatic spread after implantation of tumor cells. A comparative study of tumor growth rate of various hematopoietic cancer cell lines in different animal models shows that better growth rate is achieved in models with a B cell, T cell, NK cell, macrophage, and complement deficiency, as is exhibited in the hairless NOD scid mouse model. Additionally, the hairless NOD scid mouse has an increased metastatic potential relative to other orthotopic mouse models. The hairless NOD scid mouse is a useful model for xenographic transplant and humanization studies and has genetic and phenotypic advantages compared to scid mutants on other genetic backgrounds.

In one embodiment, a hairless, immunodeficient mouse on a non-obese diabetic (NOD) background is disclosed. The hairless immunodeficient mouse has a B-cell, T-cell, NK-cell, macrophage and complement deficiency. Further, and unexpectedly, the hairless immunodeficient mouse has a dendritic cell deficit, in that the number of dendritic cells is reduced in the hairless NOD scid mouse compared to the NOD scid mouse having hair. A reduction in dendritic cells results in a greater degree of immunodeficiency, which can be advantageous for experiments involving xenograft transplantations, spontaneous tumors, cancer cell tumorigenesis, tumor angiogenesis, tumor metastatic potential, tumor suppression therapy, carcinogenesis regulation, tumor imaging, and human stem cell engraftment.

EXAMPLES

Example

Selective Breeding to Produce Hairless NOD Scid Mice.

Mice are bred as shown is Table 1. In summary, the steps are as follows (the presence of a mutant allele is indicated by the symbol $^+$).

Step (1): Breed homozygous hairless ($Hr^{+/+}$) with homozygous NOD scid ($Prkdc^{+/+}$) mice. Preferably the Hr mice are males, because the Hr females may exhibit poor maternal characteristics. The F1 mice produced from Step 1 are all heterozygous: $Hr^{+/-}$ and $Prkdc^{+/-}$.

Step (2): Select NOD scid heterozygous males and back-cross them to NOD scid $Prkdc^{+/+}$ homozygous females. The N2 mice are a mix of genotypes. Test offspring for the presence of the Hr gene by PCR, for the presence of the Prkdc gene by single nucleotide polymorphism allelic discrimination, and NOD scid genetic background by single nucleotide polymorphism profiling.

Step (3): Select males and females with at least 80.8% NOD scid genetic background that are homozygous for Prkdc ($Prkdc^{+/+}$) and heterozygous for Hr ($Hr^{+/-}$) and breed them accordingly with NOD scid males or females.

Step (4): Test offspring for the presence of the Hr gene by PCR and for NOD scid genetic background by single nucleotide polymorphism profiling. Select males and females with at least 94% NOD scid genetic background that are homozygous for Prkdc ($Prkdc^{+/+}$) and heterozygous for Hr ($Hr^{+/-}$) and breed them accordingly with NOD scid males or females.

Step (5): Test offspring for the presence of the Hr gene by PCR and for NOD scid genetic background by single nucleotide polymorphism profiling. Select males and females with at least 99% NOD scid genetic background that are homozygous for Prkdc ($Prkdc^{+/+}$) and heterozygous for Hr ($Hr^{+/-}$) and breed them accordingly with NOD scid males or females.

Step (6): Test offspring for the presence of the Hr gene by PCR and for NOD scid genetic background by single nucleotide polymorphism profiling. Select males and females that have essentially 100% NOD scid genetic background that are homozygous for Prkdc ($Prkdc^{+/+}$) and heterozygous for Hr ($Hr^{+/-}$) and breed them accordingly with NOD scid males or females.

Step (7): Breed mice obtained from step 6 to establish a colony of hairless NOD scid. Males that are homozygous for Prkdc ($Prkdc^{+/+}$) and homozygous for Hr ($Hr^{+/+}$) may be bred with females that are homozygous for Prkdc ($Prkdc^{+/+}$) and homozygous ($Hr^{+/+}$) or heterozygous ($Hr^{+/-}$) for Hr.

TABLE 1

Schematic of Breeding to Produce Hairless NOD scid Mice

| Cross | Mice to be Mated | SNP Allelic Discrimination (scid) | Standard PCR (hr) | SNP Profiling | Comments | % Expected Genome Conversion to NOD background |
|---|---|---|---|---|---|---|
| F1 | NOD$^{scid}$ females x MF-1-hr males | No | No | No | Male heterozygous offspring are chosen for N2 cross to fix the Y chromosome | 50.0% |
| N2 | NOD$^{scid}$ females x heterozygous males | Yes | Yes | Yes | Offspring are tested for scid and hr. Females genetically more similar to NOD scid which are homozygous for scid and heterozygous for hr are chosen for N3 cross to fix the X chromosome. From this point forward, all future breeders are homozygous for scid so testing for this allele is not necessary. | 80.8% |
| N3 | NOD$^{scid}$ males x scid/scid hr/+ females AND NOD$^{scid}$ | No | Yes | Yes | Offspring are tested for hr. Males and females that are at least 80.8% NOD scid and are heterozgyous for hairless will be chosen for reciprocal matings in N4. Male mutants may be chosen first for mating to | 94.0% |

TABLE 1-continued

Schematic of Breeding to Produce Hairless NOD scid Mice

| Cross | Mice to be Mated | SNP Allelic Discrimination (scid) | Standard PCR (hr) | SNP Profiling | Comments | % Expected Genome Conversion to NOD background |
|---|---|---|---|---|---|---|
| | females X scid/scid hr/+ males | | | | increase the potential for production of offspring. | |
| N4 | NOD$^{scid}$ males x scid/scid hr/+ females AND NOD$^{scid}$ females X scid/scid hr/+ males | No | Yes | Yes | Offspring are tested for hr. Males and females that are at least 94% Nod scid and are heterozygous for hairless are chosen for reciprocal matings in N5. Male mutants may be chosen first for mating to increase the potential for production of offspring. | 99.0% |
| N5 | NOD$^{scid}$ males x scid/scid hr/+ females AND NOD$^{scid}$ females X scid/scid hr/+ males | No | Yes | Yes | Offspring are tested for hr. Males and females that are at least 99% NOD scid are mated together to produce homozygous double mutants and colony production can begin. Full sib matings should occur after this point. Initial colony future breeders may be tested for scid and hr for final confirmation and data archival. | 100.0% |

Optionally, mice with spontaneous or targeted mutations of the hairless gene other than Hr$^{hr}$ that result in the phenotype of hairlessness may be used, including but not limited to Hy$^{rh}$, Hr$^{ba}$, Hr$^{n}$, hr$^{rh8j}$, hr$^{rhChr}$, hr$^{rhsl}$, hr$^{rhy}$, hr$^{bmh}$, and hr$^{TgN5053Mm}$.

Phenotyping of Hairless NOD Scid Mice.

Hairless NOD scid mice are weighed periodically for growth curve analysis. Additionally, the mice receive standard chemistry panel and complete blood tests and bone marrow smears. Flow cytometry is used to test for the presence of B cell and T cell markers, NK cells, macrophages, and complement. Further tests include histopathology on the thymus, spleen, bone marrow, and lymph nodes, as well as skin (mammary fat pad and dermis).

Tests known to those skilled in the art are also performed to determine the immunodeficiency of the hairless NOD scid mice, including examination of immunoglobulin levels, and NK cell, macrophage, and complement activity. Mice are also monitored for the incidence of spontaneous lymphoma.

TABLE 2

Complete Blood Counts and immunoglobulin levels in hairless NOD scid mice compared to BALB/c and NOD scid

| Mouse | lymphocytes/ ul | IgG (MFI counts) | IgG (ng/ul estimate) |
|---|---|---|---|
| Hr NOD scid male | 286 | 4622 | 2-5 |
| Hr NOD scid female | 528 | 7563 | 2-5 |
| BALB/c male | 5308 | 16252 | 80 |
| BALB/c female | 8670 | 17575 | 80 |
| NOD.scid male | 1857 | 7883 | 2-5 |
| NOD.scid female | 1809 | 6109 | 2-5 |

Example

Complete Blood Counts in Hr NOD Scid Compared to NOD Scid Mice

Animals were euthanized and terminally bled for CBC and serum antibody (Ab) measurement. Routine CBCs were performed. White blood cell counts, red blood cell and platelet parameters were measured on a HEMAVET 950FS automated hematology analyzer. White blood cell differentials were obtained from a blood smear obtained at the time of blood collection. Results of this manual differential were used to calculate estimated numbers of each white blood cell type.

TABLE 3

Complete Blood Counts in hairless NOD scid mice compared to NOD scid

| | Units | Hr NOD scid (females, 6-7 weeks; n = 6) | | NOD scid (males, 6-7 weeks; n = 5) | |
|---|---|---|---|---|---|
| | | Mean | Std Dev | Mean | Std Dev |
| WBC | x103/μL | 3.6 | 1.0 | 4.2 | 0.8 |
| RBC | M/μL | 7.5 | 0.4 | 8.5 | 0.4 |
| Hgb | g/dL | 8.2 | 1.9 | 13.0 | 0.5 |
| Hct | Vol % | 41.8 | 1.8 | 47.4 | 3.0 |
| MCV | fL | 55.3 | 2.0 | 56.0 | 1.3 |
| MCH | Pg | 15.0 | 0.4 | 15.4 | 0.6 |
| MCHC | g/dL | 27.1 | 0.8 | 27.5 | 1.7 |
| Segmented Neutrophils | x103/μL | 2.6 | 0.9 | 1.7 | 1.0 |
| Segmented Neutrophils | % | 70.8 | 6.4 | 0 | 0 |
| Lymphocytes | % | 20.2 | 8.5 | 27.8 | 16.4 |
| Monocytes | % | 6.5 | 3.8 | 4.4 | 3.2 |
| Eosinophils | % | 0.1 | .0.1 | 3.8 | 3.2 |
| Platelet count | x103 | 668.8 | 167.3 | 1018.40 | 116.9 |
| MPV | fL | 4.8 | 0.1 | 4.8 | 0.1 |

Histopathology

Histpathological indices are compared between Hr NOD scid and NOD scid mice. Axillary, inguinal, cervical/mandibular, and mesenteric lymph nodes were harvested as well as spleen, thymus, mammary tissue, cecum, and pancreas. Bone marrow smears were collected from femoral bone marrow and the sternum and femur were collected for histologic analysis.

In hairless NOD scid mice, the lymph nodes and splenic white pulp appear void of cells with typical lymphocyte morphology (condensed nucleus, scant cytoplasm). The remaining visible cells are reticular support cells, dendritic cells, macrophages, and NK cells. There are varying degrees of hematopoiesis in the splenic red pulp.
Immune Cell Markers

Example

Immunoglobins Serum antibody was measured by multiplex fluorescent immunoassay (MFI). All IgG measurements for Hr NOD scid mice were less than 6.25 µg/mL, or below the threshold for leakiness in SCID models.

Example

Fluorescence Activated Cell Sorting (FACS) of surface antigens on splenocytes.

Cell surface antigens were analyzed to determine the type and level of immune cell deficits in Hr NOD scid mice compared to NOD scid mice.
Materials and Methods Splenocyte harvest. Freshly removed spleens are placed in a petri dish containing 2 ml complete RPMI-10 (450 ml RPMI-1640, 50 Ml FBS, 7.5 ml 1M HEPES, pH7.2). The spleens are cut with a scalpel blade in several places. Using a circular motion, pieces of spleen are pressed against the bottom of the petri dish with the plunger of a 5 ml syringe until mostly fibrous tissue remains. The clumps are further dispensed in the suspension by drawing up and expelling the suspension several times through a 5 ml syringe with a 20 g needle. The suspension is expelled into a Falcon 12×75 mm polypropylene tube through a cell strainer.

Removal of Red Blood Cells. Two milliliters of PHARM LYSE (diluted 1:10 in Milli-Q water) is added to the splenocyte suspension. The suspension is then immediately vortexed, and incubated 15 minutes in the dark at room temperature. The suspension is then centrifuge at 200×g for 5 minutes at 4° C. Without disturbing the pellet, the supernatant is carefully poured off and the rim of the test tube is blotted off onto paper towel. The pellet is then resuspended in 1 ml cold staining buffer. The suspension is passed through a cell strainer into a clean FALCON 12×75 mm polypropylene tube, which are kept on ice.

Cell counts. Fifty microliters Trypan Blue, 90 µl staining buffer, and 10 µl cell suspension are added in a 0.5 ml eppendorf tube. After thorough mixing, 30 µl is loaded onto a hemacytometer. Viable cells are counted on a 10× objective (viable cells appear refractile, whereas dead cells are blue). The pellet is then centrifuged at 350×g for 5 minutes and then resuspended to a suitable final volume ($1 \times 10^6$ cells per 200 µl sample for FACS analysis) and aliquoted into 1.5 ml tubes.

Fluorescent Immunostaining for Cell Surface Antigens. The cells are immunostained with fluorochrome-conjugated monoclonal antibodies specific for a cell surface antigen. Cells are incubated with antibodies for 30 minutes at 4° C. in the dark. Then, they are pelleted by centrifugation at 500×5 for 5 minutes, followed by resuspension in 500 µl cold staining buffer and transfer to FALCON 12×75 mm polystyrene tubes. Visible clumps are removed prior to FACS analysis.

TABLE 4

The antibodies are as follows:

| BD product # | Description | Lot # | [Ab] | Working [Ab] | Dilution | ul to Add |
|---|---|---|---|---|---|---|
| 553047 | CD4, FITC | 62786 | 0.5 mg/ml | 0.06 µg | 1:10 | 1.2 |
| 557399 | CD19, PE | 52658 | 0.2 mg/ml | 0.06 µg | 1:10 | 3.0 |
| 553858 | DX5/CD49B, PE | 34389 | 0.2 mg/ml | 1.0 µg | None | 5.0 |
| 553033 | CD8α, PE | 64081 | 0.2 mg/ml | 0.06 µg | 1:10 | 3.0 |
| 553066 | CD3e, APC | 60549 | 0.2 mg/ml | 1.0 µg | None | 5.0 |
| 550261 | CD11c, APC | 62529 | 0.2 mg/ml | 0.25 µg | None | 1.25 |
| 553047 | CD4, FITC | 62786 | 0.5 mg/ml | 0.06 µg | 1:10 | 1.2 |
| 553066 | CD3e, APC | 60549 | 0.2 mg/ml | 1.0 µg | None | 5.0 |
| 553033 | CD8α, PE | 64081 | 0.2 mg/ml | 0.06 µg | 1:10 | 3.0 |
| 553066 | CD3e, APC | 60549 | 0.2 mg/ml | 1.0 µg | None | 5.0 |
| 553858 | DX5/CD49B PE | 34389 | 0.2 mg/ml | 1.0 µg | None | 5.0 |
| 553066 | CD3e, APC | 60549 | 0.2 mg/ml | 1.0 µg | None | 5.0 |
| 553929 | CD4:Rat IgG2a, FITC | 40513 | 0.5 mg/ml | 1.0 µg | None | 2.0 |
| 553930 | CD19:Rat IgG2a, PE | 58248 | 0.2 mg/ml | 1.0 µg | None | 5.0 |
| 553943 (553930) | DX5:Rat IgM, PE Same as CD19 IC | 55080 | 0.2 mg/ml | 1.0 µg | None | 5.0 |
| 553974 | Ham, IgG1κ, APC | 66673 | 0.2 mg/ml | 1.0 µg | None | 5.0 |
| 553956 | Ham, IgG1λ, APC | 62842 | 0.2 mg/ml | 1.0 µg | None | 5.0 |

Results

Figure 1:
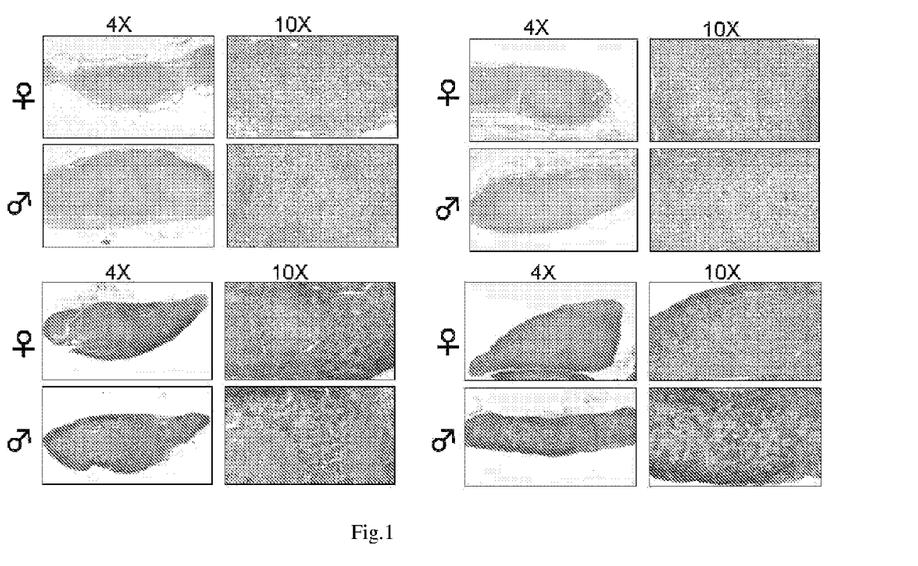
FIG. 1 shows histology sections of mesenteric lymph nodes (top) and spleens (bottom) of male and female NOD scid and Hr NOD scid mice.
Figure 2:
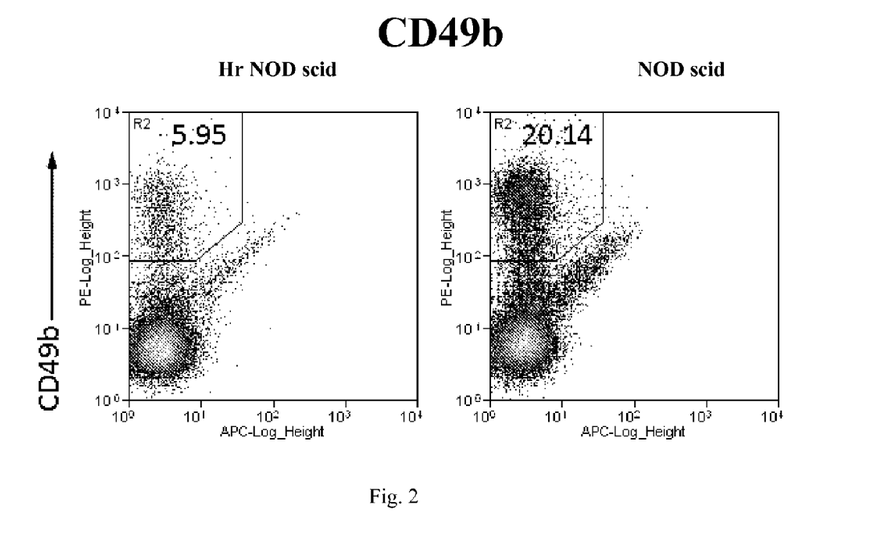
FIG. 2 shows dot plots of flow cytometry (FACS) results for CD49b. The numbers in the quadrants are mean percentages.
Figure 3:
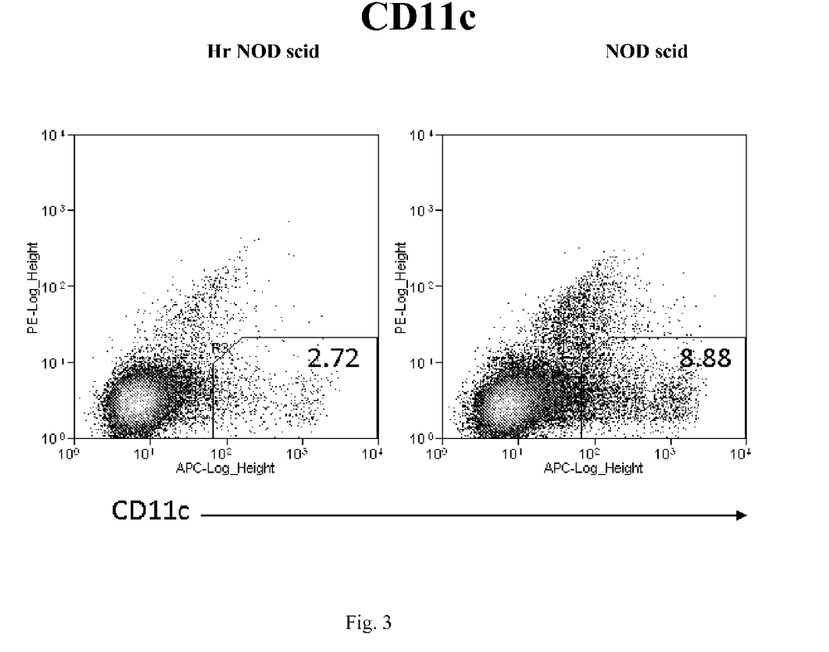
FIG. 3 shows dot plots of flow cytometry (FACS) results for CD11c. The numbers in the quadrants are mean percentages.
Figure 4:
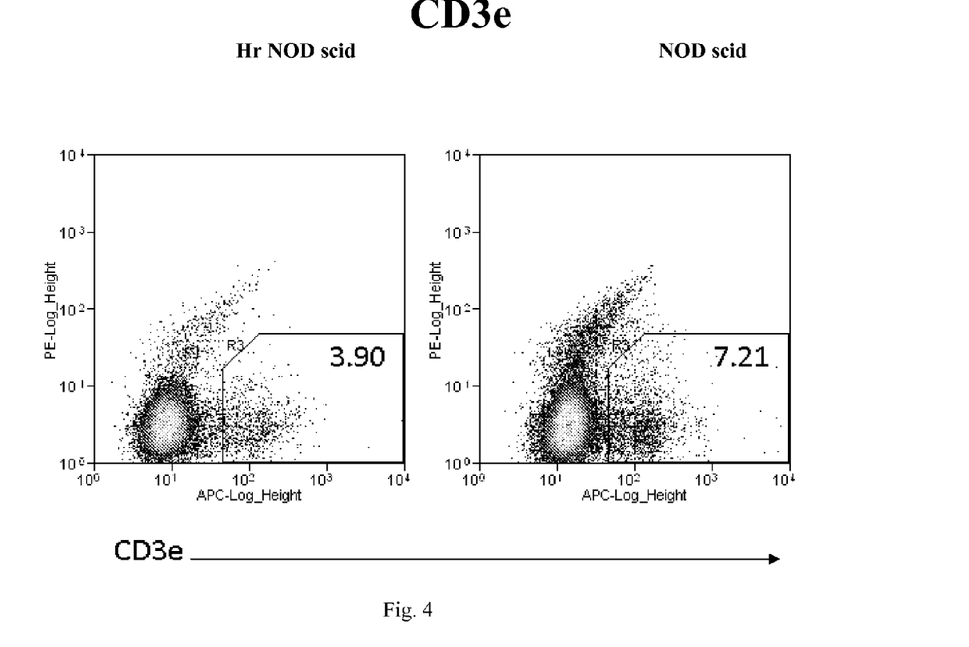
FIG. 4 shows dot plots of flow cytometry (FACS) results for CD3e and CD49b. The numbers in the quadrants are mean percentages.
Figure 5:
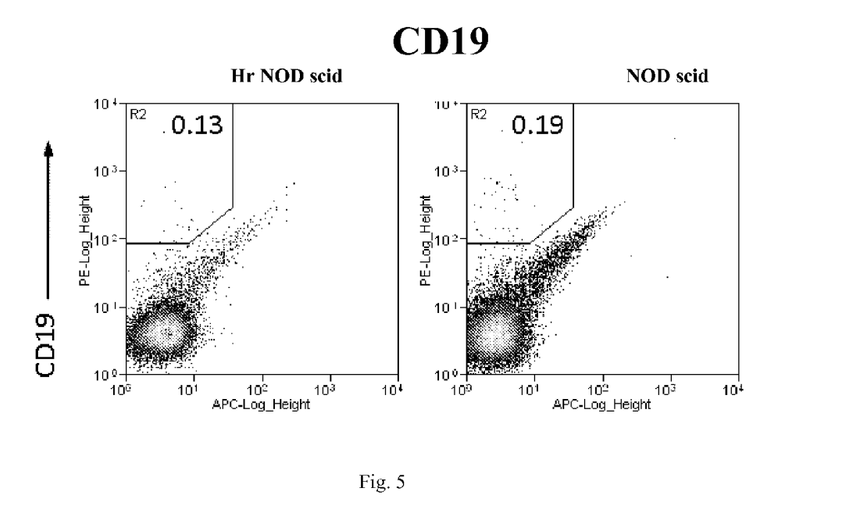
FIG. 5 shows dot plots of flow cytometry (FACS) results for CD3e and CD49b. The numbers in the quadrants are mean percentages.
Figure 6:
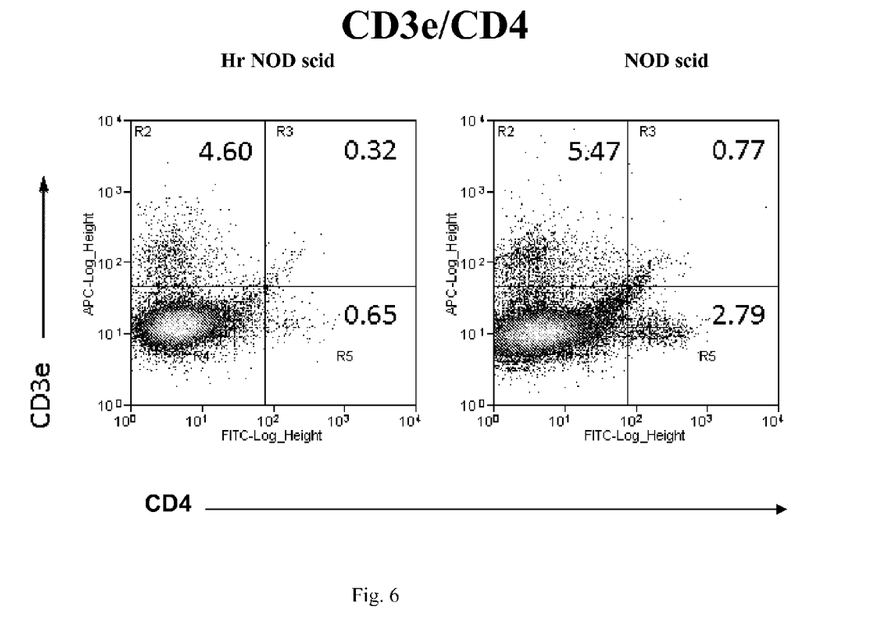
FIG. 6 shows dot plots of flow cytometry (FACS) results for CD3e and CD8a. The numbers in the quadrants are mean percentages.
Figure 7:
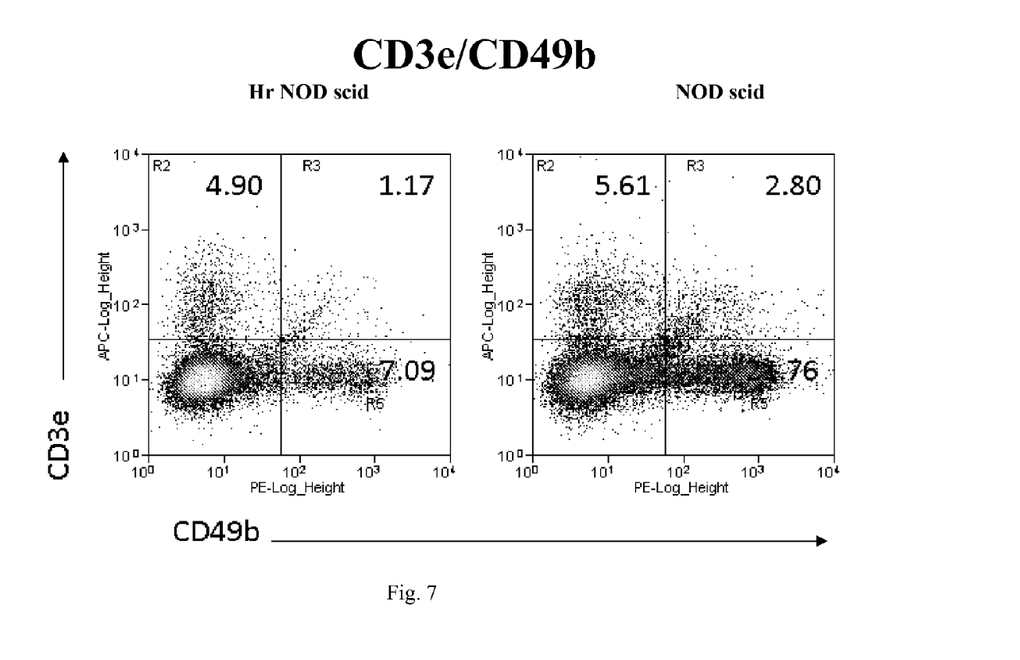
FIG. 7 shows dot plots of flow cytometry (FACS) results for CD49b. The numbers in the quadrants are mean percentages.
Figure 8:
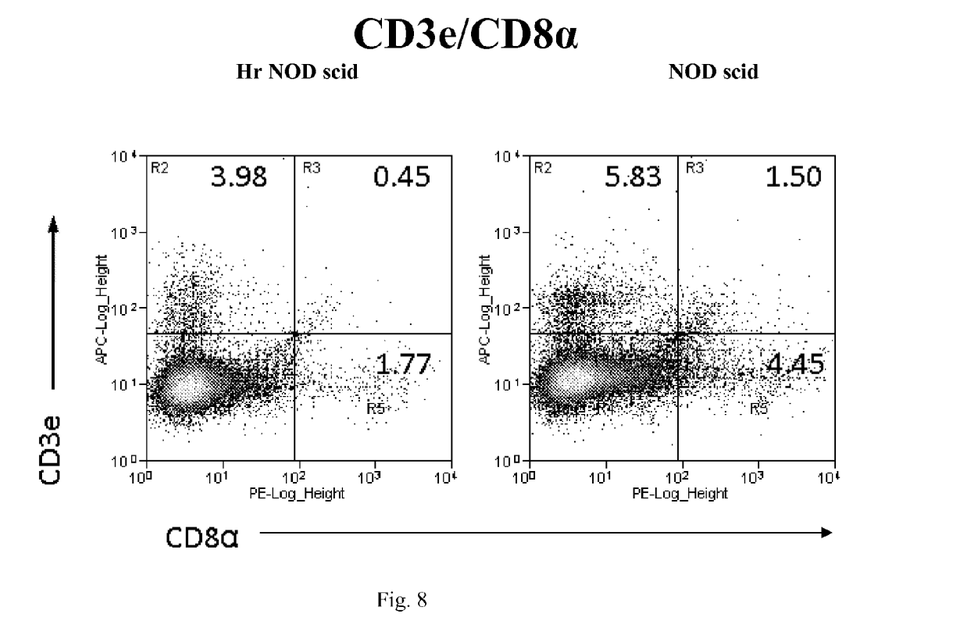
FIG. 8 shows dot plots of flow cytometry (FACS) results for CD49b. The numbers in the quadrants are mean percentages.

Flow cytometry analysis confirmed that the Hr NOD scid mice were nearly completely lacking T-cells and B-cells. CD 19, a common B-cell lineage marker, showed that both strains were nearly devoid of mature B cells (FIG. 5). The Hr NOD scid mice had fewer lymphocytes overall than NOD scid mice. In particular NK cells (FIG. 2) and dendritic cells (FIG. 3) in the Hr NOD scid mice were markedly decreased in comparison to the NOD scid. Statistically significant differences were found between the T- and NK-cell sup-populations as well as the dendritic cells of both strains. Flow cytometry data was analyzed in two-way ANOVA using SAS. P-values of 0.05 or less were indicative of significant variance (Hr NOD scid, n=12; NOD scid, n=10).

Positive staining for cell surface antigens of the table below is used to distinguish various types of immune cells.

TABLE 5

| Cell Surface Antigen | Cell Type |
|---|---|
| CD3e | T-cells |
| CD4 | helper T-cells |
| CD8α | cytotoxic T-cells |
| CD11c | dendritic cells |
| CD19 | B-cells |
| CD49b | NK cells |

Example

Xenograft Of Tumorigenic Cell Lines

Tumorigenic cell lines derived from cancers of bladder, breast, head and neck, colon, blood, liver, lung, melanoma, ovary, pancreas, prostate, or testes are transplanted to hairless NOD scid mice according to procedures known in the art. The following cell lines are tested for ability to be uptaken and grow in hairless NOD scid mice: HTLA-230 (Brignole et al., 2004), CT-26 (Guba et al., 2001), BW5147 (Geldhof et al., 1998), Grant 519 (Wang et al., 2007), Karpas 299 (Francisco et al., 2003), L540cy (Francisco et al., 2003, Colo-699 (Boehle et al., 2001), SIT1 (Bromberg et al., 2005), TAC 7 (Bromberg et al., 2005), DU-145 (Glinskii et al., 2005).

Human large cell lymphoma cell line KARPAS-299 and mantle cell lymphoma cell line JEKO-1 is purchased from ATCC. KARPAS-299 cells are cultured in RPMI 1640 with 10% FBS, JEKO-1 cells in RPMI 1640 as well, with 20% FBS. Female mice at approximately eight weeks of age are subcutaneously inoculated with $1.0 \times 10^7$ cells with Matrigel in a 1:1 dilution with cell suspension.

Figure 9:
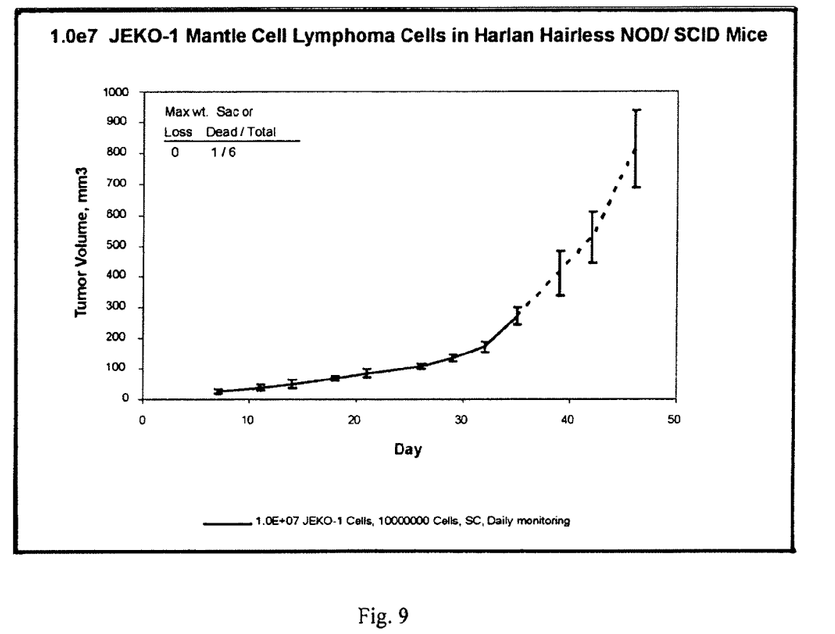
FIG. 9 shows tumor development from human mantle cell lymphoma cell line JEKO-1 xenotransplanted in Hr NOD scid mice.
Figure 10:
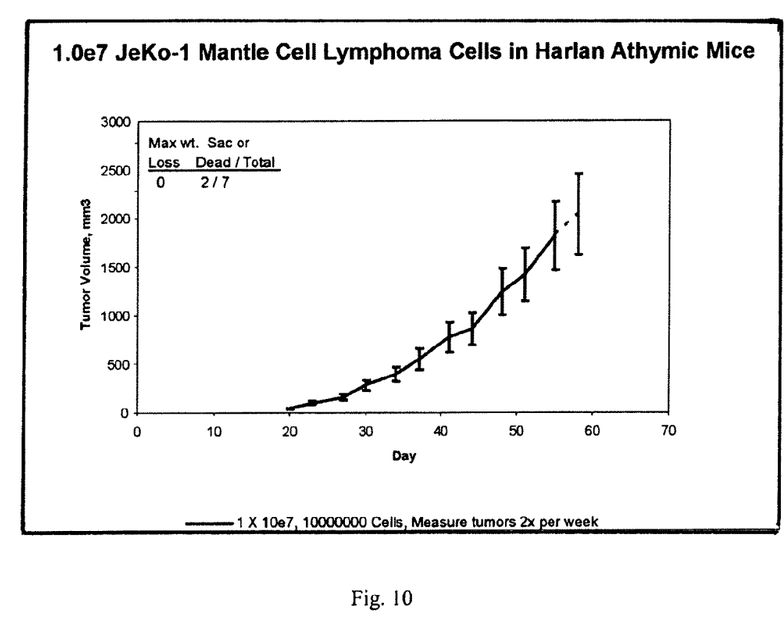
FIG. 10 shows tumor development from human mantle cell lymphoma cell line JEKO-1 xenotransplanted in athymic nude mice.
Figure 11:
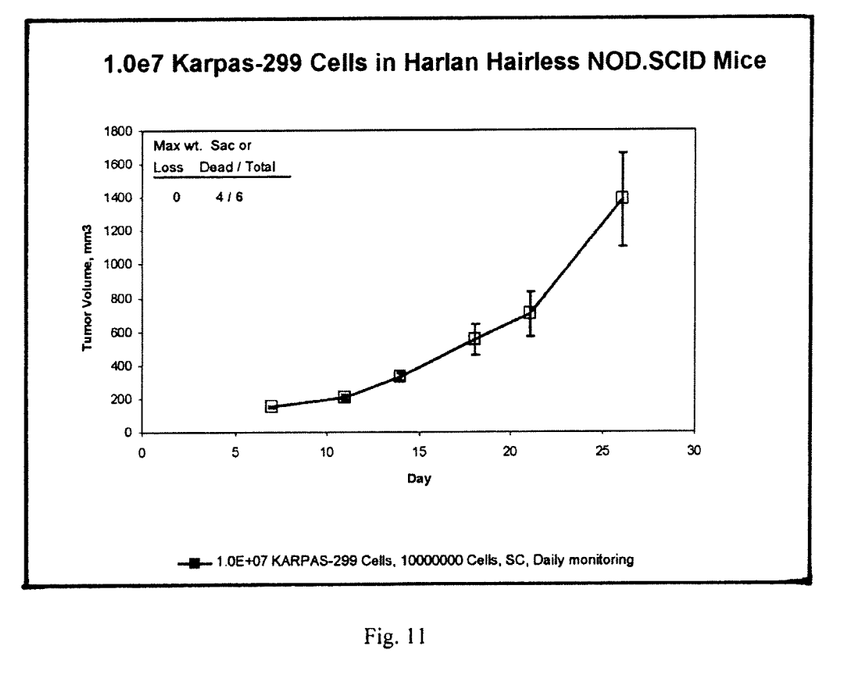
FIG. 11 shows tumor development from human large cell lymphoma cell line KARPAS-299 xenotransplanted in Hr NOD scid mice without whole body irradiation.

The KARPAS-299 cell line will not grow in athymic mice without whole body irradiation. In contrast, the Hr NOD scid model exhibited robust growth with subcutaneous injection without irradiation (FIG. 11). The JEKO-1 tumor cell line can be successfully transplanted into athymic nude mice whether or not they are irradiated prior to inoculation, though initial proliferation is slow. In this study, the athymic nude mice had approximately 25-27 days lag time to log-phase growth (FIG. 9), whereas the Hr NOD scid mouse showed rapid and vigorous growth (FIG. 10). Indeed, all Hr NOD scid mice developed tumors within 14 days post inoculation.

Additional cell lines are tested for uptake and growth in hairless NOD scid mice including: U251-NG, MCF-7, MDA-MB-231, T47D, CX-1, DLD-1, HAC-7, HC116, HT-29, FaDu, HNX-OE, A549, H322, H358, LL2, NCI-8460, NC1-N417, B16F10, MOT, OVCAR3, CFPAC-1, Colo57, Mla-Paca-2, PANC-1, PL45, CWR22, LNAI, PC-3, NCCIT, T24, G55, U87MG, SH-SY5Y, MCF-7, MT-1, HPB-ALL, HepT1, Hep3B, HuH6, and SKOV3. The ability of other cell types to thrive upon implantation, such as stem cells (expressing CD34), is also tested.

Other mouse strains such as NOD scid, athymic nude, MF-1 hairless, CB.17, BALB/c and the like may be included in experiments for comparative purposes.

Using single nucleotide polymorphism (SNP) marker-assisted backcrossing methodology, a hairless mutation ($Hr^{hr}$) has been transferred from an outbred HsdOla:MF1-$Hr^{hr}$ to the NOD.CB17-Prkdc$^{scid}$/NCrHsd mouse to generate the inbred hairless NOD.Cg-Prkdc$^{scid}$Hr$^{hr}$/NCrHsd mouse, commonly named hairless NOD scid The immunologic characteristics of this model are herein described, which include B and T cell deficiency, a functional deficit of NK cells, and decreased macrophage and complement function. In addition, it is discovered herein that NK cells and dendritic cells are substantially reduced in Hr NOD scid mice compared to NOD scid.

While the invention has been illustrated and described in detail in the foregoing description, such an illustration and description is to be considered as exemplary and not restrictive in character, it being understood that only the illustrative embodiments have been described and that all changes and modifications that come within the scope of the invention are desired to be protected. Those of ordinary skill in the art may readily devise their own implementations that incorporate one or more of the features described herein, and thus fall within the scope of the present invention.

References

Baersch G, Mollers T, Hotte A, Dockhorn-Dworniczak B, Rube C, Ritter J, Jurgens H, Vormoor J (1997) Good engraftment of B-cell precursor ALL in NOD-SCID mice. *Klin Padiatr* 209:178-85.

Bastide C, Bagnis C, Mannon P, Hassoun, J, and Bladou F (2002) A Nod Scid mouse model to study human prostate cancer. *Prostate Cancer and Prostatic Diseases,* 5:311-5.

Boehle A S, Kurdow R, Schulze M, Kliche U, Sipos B, Soondrum K, Ebrahimnejad A, Dohrmann P, Kalthoff H, Henne-Bruns D, Neumaier M (2001) Human endostatin inhibits growth of human non-small-cell lung cancer in a murine xenotransplant model. *Int J Cancer* 94(3):420-8.

Bosma M J, and Carroll A M (1991) The Scid Mouse Mutant: Definition, Characterization, and Potential Uses. *Ann. Rev. Immunol.* 9:323-50.

Brignole C, Pastorino F, Marimpietri D, Pagnan G, Pistorio A, Allen T M, Pistoia V, and Ponzoni M (2004) *J. Natl. Cancer Inst.* 96:1171-1180.

Bromberg M E, Konigsberg W H, Madison J F, Pawashe A, Garen A (2005) Tissue factor promotes melanoma metastasis by a pathway independent of blood coagulation. *Proc. Natl. Acad. Sci. USA* 92:8205-8209.

Christianson S W, Greiner D L, Schweitzer I B, Gott B, Beamer G L, Schweitzer P A, Hesselton R M, Shultz L D (1996) Role of natural killer cells on engraftment of human lymphoid cells and on metastasis of human T lymphoblastoid leukemia cells in C57BL/6J-scid mice and in C57BL/6J-scid bg mice. *Cell Immunol* 171:186-199.

Crew F A E and Mirskaia L (1931) The character "hairless" in the mouse. *J. Genet.* 25:17-24.

Francisco J A, Cerveny C G, Meyer D L, Mixan B J, Klussman K, Chace D F, Rejniak S X, Gordon K A, DeBlanc R, Toki B E, Law C L, Doronina S O, Siegall C B, Senter P D, and Wahl A F (2003) cAC10-vcMMAE, an anti-CD30-monomethyl auristatin E conjugate with potent and selective antitumor activity. *Blood* 102(4):1458-1465.

Fraser F C (1946) The expression and interaction of hereditary factors producing hypotrichosis in the mouse: Histology and experimental results. *Canad. J. Res.* 24:10-25.

Fukui M, Ito K, Kawamura S, Sudo K, Susuki K, Shimizu F (1975) Glomerular changes in hairless mice: a light, immunofluorescent and electron microscopic study. *Japan J. Exp. Med.* 45:535-540.

Geldhof A B, Van Ginderachter J, Vandersteen P, Raes G, De Baetselier P (1998) Multiple effects of transfection with interleukin 2 and/or interferon gamma on the behavior of mouse T lymphoma cells. *Clinical & Experimental Metastasis* 16(5):447-59.

Glinskii O V, Huxley V H, Glinsky G V, Pienta K J, Raz A, Glinsky V V (2005) Mechanical entrapment is insufficient and intercellular adhesion is essential for metastatic cell arrest in distant organs. *Neoplasia* 7(5):522-27.

Greiner D L, Hesselton R A, Shultz L D (1998) SCID mouse models of human stem cell engraftment. *Stem Cells* 16(3):166-77.

Guba M, Cernaianu G, Koehl G, Geissler E K, Jauch K W, Anthuber M, Falk W, Steinbauer M (2001) A primary tumor promotes dormancy of solitary tumor cells before inhibiting angiogenesis. *Cancer Res.* 61(14):5575-79.

Heiniger H J, Meier H, Kalis N, Cherry M, Chen H W, Stoner R D (1974) Hereditary immunodeficiency and leukogenesis in HRS/J mice. *Cancer Res.* 34:201-211.

Institute for Laboratory Animal Research (1989) *Immunodeficient rodents. A guide to their immunobiology, husbandry, and use*. National Academy Press, Washington D.C.

Johnson D A, Meier H (1981) Immune responsiveness of HRS/J mice to syngeneic lymphoma cells. *J. Immunol.* 127:461-464.

L'Anson V A and Gasser D L (1973) Relationship between graft-vs-host reactivity and possession of the high leukaemia genotype hr/hr. *J. Immunol.* 111:1604-1611

Larochelle A, Vormoor J, Hanenberg H, Wang J C Y, Bhatia M, Lapidot T, Moritz T, Murdoch B, Xiao X L, Kato I, Williams D A, and Dick J E (1996) Identification of primitive human hematopoietic cells capable of repopulating NOD/SCID mouse bone marrow: implications for gene therapy. *Nat. Med.* 2:1329-37.

Lyon M F, Rastan S. and Brown S D M. (Eds). (1996) *Genetic Variants and Strains of the Laboratory Mouse*. Third Edition, Volume 1. Oxford: Oxford University Press.

Makino S, Kunimoto K, Muraoka Y, Mizushima Y, Katagiri K, and Tochino Y (1980) Breeding of a non-obese, diabetic strain of mice. *Exp. Anim.* 29:1-8.

Mann S J (1971) Hair loss and cyst formation in hairless and rhino mutant mice. *Anat. Rec.* 170:485-500.

Morrisey P J, Parkinson D R, Schwartz R S, Waksal S D (1980) Immunological abnormalities in HRS/J mice. I. Specific deficit in T lymphocyte helper function in a mutant mouse. *J. Immunol.* 125:1558-1562.

Nonoyama S, Smith F O, Bernstein I D, Ochs H D (1993) Strain-dependent leakiness of mice with severe combined immune deficiency. *J Immunol* 150:3817-24.

Pelsue S C, Leif J, Rajan T V (1995) Improved engraftment of human spleen cells in NOD/LtSz-scid/scid mice as compared with C.B-17-scid/scid mice. *Am J Path* 146:888-902.

Potter G B, Beaudoin G M 3rd, DeRenzo C L, Zarach J M, Chen S H, Thompson C C (2001) The hairless gene mutated in congenital hair loss disorders encodes a novel nuclear receptor corepressor. *Genes Dev.* 15(20):2687-2701.

Reske-kunz A B, Scheid M P, and Boyse E A (1979) Disproportion in T-cell subpopulations in immunodeficient mutant hr/hr mice. *J Exp Med* 149:228-233.

Shultz L D, Schweitzer P A, Christianson S W, Gott B, Schweitzer I B, Tennent B, McKenna S, Mobraaten L, Rajan T V, and Greiner D L (1995) Multiple defects in innate and adaptive immunologic function in NOD/LtSz-scid mice. *J. Immunol.* 154:180-91.

Wang J C Y, Lapidot T, Cashman J D, Doedens M, Addy L, Sutherland D R Nayar R, Laraya P, Minden M, Keating A, Eaves A C, Eaves C J, Dick J E (1998) High level engraftment of NOD/SCID mice by primitive normal and leukemic hematopoietic cells from patients with chronic myeloid leukemia in chronic phase. *Blood* 91(7):2406-2414.

Wang M, Zhang L, Han X, Yang J, Qian J, Hong S, Samaniego F, Romaguera J, and Yi Q (2007) Atiprimod inhibits the growth of mantle cell lymphoma in vitro and in vivo and induces apoptosis via activating the mitochondrial pathways. *Blood* 109:5455-5462.

What is claimed is:

1. A method of producing a transgenic, hairless, immunodeficient mouse whose genome comprises a homozygous $Prkdc^{scid}$ mutation and a homozygous $Hr^{hr}$ mutation on a non-obese diabetic NOD.CB17 background, the method comprising:
    (a) crossing a homozygous NOD.CB17-$Prkdc^{scid}$ mouse with a homozygous MF-1-hr mouse to produce a progeny that is heterozygous for both the Hr allele and the Prkdc allele;
    (b) crossing the heterozygous progeny produced from step (a) with NOD.CB17-$Prkdc^{scid}$ mice;
    (c) selecting an offspring of step (b) that has a NOD.CB17 background, is homozygous for the Prkdc allele, and is heterozygous for the Hr allele;
    (d) crossing the offspring selected in step (c) with mice homozygous or heterozygous for the Hr allele to obtain a homozygous NOD.CB17-$Prkdc^{scid}$ $Hr^{hr}$ double mutant transgenic mouse,
    wherein the NOD.CB17-$Prkdc^{scid}$ $Hr^{hr}$ double mutant transgenic mouse exhibits B-cell, T-cell, NK-cell, macrophage, and complement deficiencies, and a reduction in the number of dendritic cells compared to an immunodeficient mouse of a NOD.CB17-$Prkdc^{scid}$ background that is not hairless.

2. A transgenic, hairless, immunodeficient mouse whose genome comprises a homozygous $Prkdc^{scid}$ mutation and a homozygous $Hr^{hr}$ mutation on a non-obese diabetic NOD.CB17 background,
    wherein the mouse exhibits B-cell, T-cell, NK-cell, macrophage, and complement deficiencies and a reduction in the number of dendritic cells compared to an immunodeficient mouse of a NOD.CB17-$Prkdc^{scid}$ background that is not hairless.

* * * * *